United States Patent [19]

Lee et al.

[11] Patent Number: 4,996,353
[45] Date of Patent: Feb. 26, 1991

[54] PROCESS FOR THE PREPARATION OF PARA,PARA'-POLYPHENYLDICARBOXYLIC ACID

[75] Inventors: Guo-shuh J. Lee; Kenneth A. Burdett; Joseph J. Maj, all of Midland, Mich.

[73] Assignee: The Dow Chemical Company, Midland, Mich.

[21] Appl. No.: 352,575

[22] Filed: May 16, 1989

[51] Int. Cl.$^5$ ............................................. C07C 51/215
[52] U.S. Cl. ..................... 562/412; 562/416; 562/417
[58] Field of Search .................... 562/412, 416, 417

[56] References Cited

U.S. PATENT DOCUMENTS

| | | | |
|---|---|---|---|
| 3,139,452 | 6/1964 | Hay | 562/416 |
| 3,644,506 | 2/1972 | Williamson | 562/416 |
| 3,870,754 | 3/1975 | Yamashita et al. | 562/417 |
| 4,197,412 | 4/1980 | Kimura et al. | 562/416 |
| 4,314,073 | 2/1982 | Crooks | 562/416 |
| 4,582,925 | 4/1986 | Donohue | 560/76 |
| 4,709,088 | 11/1987 | Hirose et al. | 562/414 |
| 4,786,753 | 11/1988 | Partenheimer et al. | 562/416 |

FOREIGN PATENT DOCUMENTS

| | | |
|---|---|---|
| 0204119 | 12/1986 | European Pat. Off. . |
| 0267774 | 5/1988 | European Pat. Off. . |
| 77003377 | 10/1969 | Japan . |
| 63-063638 | 3/1988 | Japan . |
| 63-122648 | 5/1988 | Japan . |
| 63-310846 | 12/1988 | Japan . |
| 2187744 | 9/1987 | United Kingdom . |

*Primary Examiner*—Werren B. Lone
*Assistant Examiner*—Vera C. Clarke

[57] ABSTRACT

A process for the preparation of polyphenyl dicarboxylic acids is disclosed. The process comprises contacting para,para'-diisoalkyl or dialkyl-polyphenyl or an oxidation intermediate thereof with oxygen under reaction conditions sufficient to form para,para'-polyphenyldicarboxylic acid. The process is optionally carried out in the presence of cobalt, manganese, and bromine compounds.

14 Claims, No Drawings

PROCESS FOR THE PREPARATION OF PARA,PARA'-POLYPHENYLDICARBOXYLIC ACID

BACKGROUND OF THE INVENTION

This invention relates to a process for the preparation of carboxylic acids from the corresponding isoalkyl compounds. More specifically, this invention relates to a process for the preparation of para,para'-polyphenyldicarboxylic acid. Para,para'-polyphenyldicarboxylic acid is useful as a raw material for the production of high-performance polyesters and aramid resins having high heat resistance and strength.

EPO application No. 206,543 discloses a process for coupling haloaromatic carboxylic acid compounds in the presence of carbon monoxide, an aqueous solution of an alkali metal hydroxide, and a supported palladium catalyst to form 4,4'-biphenyldicarboxylic acid. U.S. Pat. No. 3,644,506 describes a process for the preparation of aromatic carboxylic acids which comprises oxidizing aromatic compounds containing at least one methyl substituent in the presence of a cobalt, manganese, nickel, or chromium catalyst, wherein the water content of the reaction mixture is maintained at less than 0.9 percent by weight throughout the reaction period.

As illustrated in the examples hereinbefore, the syntheses of polynuclear aromatic dicarboxylic acids requires considerable effort. In view of this and other deficiencies of the aforementioned prior art processes, it is desirable to provide an alternate route for the production of polynuclear aromatic dicarboxylic acids which will simplify the synthesis of such compounds and their derivatives.

SUMMARY OF THE INVENTION

This invention is a process for the preparation of para,para'-polyphenyldicarboxylic acid which comprises contacting a para,para'-diisoalkyl- or dialkyl-polyphenyl compound or an oxidation intermediate thereof with oxygen under reaction conditions sufficient to form a para,para'-polyphenyldicarboxylic acid.

DETAILED DESCRIPTION OF THE INVENTION

Diisoalkyl- or dialkyl-polyphenyl compounds for use in the process of this invention may be prepared by the alkylation of a polyphenyl compound using an acid catalyst. One example of such a method is described in copending U.S. application Ser. No. 123,741 of G. J. Lee et al., "Alkylation of Polycyclic Aromatic Compounds to Alkylates Enriched in the Para-Substituted Isomers," filed Nov. 23, 1987, the relevant portions of which are hereby incorporated by reference.

The term "diisoalkyl- or dialkyl-polyphenyl compounds" as used herein refers to para-substituted biphenyl, para-substituted terphenyl, or para-substituted para-phenoxybiphenyl compounds having two isopropyl or isobutyl groups, or one of each, and are preferably compounds of the following formula:

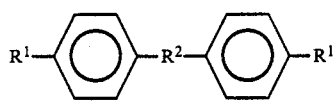

wherein $R^1$ is independently in each occurrence methyl, ethyl, isopropyl, isobutyl, $C_{3-10}$ n-paraffins or cycloparaffins, or $C_{5-10}$ isoparaffins, and $R^2$ is phenylene, phenoxylene, phenylenedioxy, or a chemical bond. $R^1$ is preferably isopropyl or isobutyl, and most preferably is isopropyl. Examples of such compounds include para,para'-diisopropylbiphenyl compounds, 4,4'-diisobutylbiphenyl compounds, and 4-isopropyl-4'-isobutylbiphenyl compounds.

The term "oxidation intermediate of para,para'-diisoalkli- or dialkyl-polyphenyl" as used herein means a derivative formed by the oxidation of para,para'-diisoalkyl- or dialkyl-polyphenyl which forms a para,para'-polyphenyldicarboxylic acid upon further oxidation. Examples of such intermediates are 4'-isopropylbiphenyl-4-carboxylic acid, 4'-iso-propylbiphenyl-4-carbinolbiphenyl, 4'-isopropylbiphenyl-4-dihydroperoxyalkylbiphenyl, and 4'-isopropylbiphenyl-4-diformylbiphenyl.

The process of the invention is preferably carried out in the presence of a solvent medium comprising at least 50 weight percent of any organic solvent stable under the oxidation conditions of the process of the invention. Preferably, the solvent is benzene, a $C_{6-10}$ paraffin, or an aliphatic $C_{1-3}$ monocarboxylic acid or an aromatic monocarboxylic acid. Examples of such aliphatic $C_{1-3}$ monocarboxylic acids include formic acid, acetic acid, and propionic acid, with propionic acid as the most preferred. In a second preferred embodiment, the use of an aromatic monocarboxylic acid, such as benzoic acid, is preferred for its better thermal stability under oxidation conditions. The solvent to be used may be mixed with water as desired, although it is preferable to reduce the amount of water in the reaction mixture as much as possible, since it may reduce the oxidation rate of the reaction.

The solvent medium is preferably employed in an amount of about 0.5-20 times by weight, more preferably about 1-5 times by weight, of the total amount of the para,para'-diisoalkyl- or dialkyl-polyphenyl, or oxidation intermediate thereof employed. The use of smaller quantities of solvent hinders the flowability and reactivity of the reaction mixture, whereas larger amounts of solvent may not result in any increased reactivity, although it will advantageously result in a purer product. Similarly, the continuous addition of small quantities of starting material to a stirred tank reactor will result in a purer product.

The process of the invention is preferably carried out in the presence of an effective amount of at least one oxidation catalyst, which is preferably a cobalt catalyst. Preferably, the cobalt catalyst is employed in a mixture of cobalt, manganese, and bromine compounds, due to their combined catalytic effect. Any cobalt or manganese salt or compound that is soluble in the oxidation reaction mixture may be employed. For example, inorganic salts of cobalt or manganese such as oxides, hydroxides, carbonates, and halides may be employed. In addition, cobalt or manganese organic salts such as, for example, salts of carboxylic acids including formic acid, acetic acid, propionic acid, fatty acids, naphthenic acids; aromatic carboxylic acids including benzoic acid may also be used. Preferred cobalt and manganese compounds are cobalt and manganese acetates, with cobalt acetate tetrahydrate and manganese acetate tetrahydrate being the most preferred catalysts. The cobalt and manganese compounds are preferably used in combination with each other.

Suitable bromine compounds are soluble in the oxidation reaction mixture and are preferably selected from the groups consisting of molecular bromine, hydrogen bromide, metal bromides, ammonium bromide, and hydrobromide salts such as pyridinium hydrobromide, as well as organic compounds such as ethyl bromide and bromoacetic acid. Hydrogen bromide, potassium bromide, and ammonium bromide are more preferred, with potassium bromide being the most preferred.

If cobalt is used, it is preferably present in an amount in the range of from about 0.5 to about 0.01 moles of cobalt per mole of starting material Although the oxidation rate increases with increased amounts of cobalt, concentrations higher than the suggested range may be difficult to remove from the polyphenyldicarboxylic acid product, and may cause discoloration of the product and oxidation of the organic solvent. If a manganese compound is used, it is preferably present in an amount in the range from about 0.5 to about 0.01 moles of manganese per mole of starting material If a bromine compound is used, it is preferably present in an amount sufficient to provide about 0.5 to about 0.01 moles of bromine per mole of starting material. The selectivity to para,para'-polyphenyldicarboxylic acid improves as the amount of bromine compound utilized increases, although they are preferably not used in an amount greater than will dissolve in the oxidation reaction mixture.

The oxidation process may be carried out in any suitable oxidation reaction vessel, such as a titanium reactor, into which an oxygen-containing inert gas may be introduced. This process may be carried out with the use of essentially pure oxygen or mixture of oxygen with inert gases. Air is generally used as the source of oxygen according to the process of this invention. The oxidation process may be carried out at any pressure above the vapor pressure of the reaction mixture, as long as the solvent will remain in liquid phase at the reaction pressure. The oxygen partial pressure is preferably above about 10 psig, more preferably above about 50 psig, and most preferably above about 100 psig. Higher reaction pressures increase the rate of oxidation, and upper limits on reaction pressures are advantageously determined by the safety of the process equipment, although the reaction pressure is preferably below about 500 psig, and more preferably below about 200 psig to avoid decomposition of the process materials. Preferably, the oxygen-containing inert gas is fed continuously to the reactor, and a condenser used to prevent the loss of solvent. The oxidation process may be carried out at any temperature which will allow the oxidation of the polyphenyl compound to proceed. The reaction temperature is preferably above about 100° C., more preferably above about 120° C., and most preferably above about 150° C., and is preferably below about 240° C., more preferably below about 230° C. and most preferably below about 190° C. Below these ranges, the oxidation rate is very slow. Above these ranges, some of the solvent will be oxidized to carbon dioxide.

The crude oxidation product may be decolorized, if so desired, by dissolving the product in an aqueous 3 percent NaOH solution and filtering the solid therefrom. The filtrate may then be neutralized with concentrated (2N) aqueous HCl to yield an off-white product. This purified oxidation product is of sufficient purity for use in the manufacture of polyesters.

Illustrative Embodiments

The following examples are given to illustrate the invention and should not be interpreted as limiting it in any way. Unless stated otherwise, all parts and percentages are given by weight.

Example 1 - Preparation of 4,4'-Biphenyldicarboxylic Acid

A 440-g portion of acetic acid, 1.25 g (0.0033 mole) of cobalt acetate tetrahydrate, 1.23 g (0.0033 mole) of manganese acetate tetrahydrate, 0.6 g (0.005 mole) of potassium bromide, 1.48 g (0.015 mole) of potassium acetate and 10 g (0.042 mole) of 4,4'-diisopropylbiphenyl are charged to a one-liter stirred titanium autoclave, which is then sealed. The reactor is then heated to 150° C., and 60 psig oxygen is introduced into the reactor to bring the total reactor pressure to about 150 psig. The reactor temperature is then raised to 180° C. and held for one hour. The reactor is then cooled to 50° C. and the carbon dioxide generated from oxidation is vented. The reactor is heated again to 180° C., and oxygen introduced into the reactor and the temperature held for one hour. This procedure is repeated three more times. The reactor is cooled to room temperature and the contents filtered. A solid is obtained and washed with water and acetone to yield 9.4 g of a light brown solid, which is identical to 4,4'-biphenyldicarboxylic acid by infrared analysis. The yield of 4,4'-biphenyldicarboxylic acid is about 92 percent.

What is claimed is:

1. A process for the preparation of para,para'-polyphenyldicarboxylic acid which comprises contacting para,para'-diisopropyl or diisobutyl-polyphenyl or an oxidation intermediate thereof with oxygen under reaction conditions sufficient to form para,para'-polyphenyldicarboxylic acid.

2. The process of claim 1 wherein the para,para'-polyphenyldicarboxylic acid is para,para'-biphenyldicarboxylic acid, para,para'-terphenyldicarboxylic acid, para,para'-phenoxybiphenyldicarboxylic acid, or para,para'-biphenoxyphenyldicarboxylic acid.

3. The process of claim 1 wherein the para,para'-polyphenyldicarboxylic acid is 4,4'-biphenyldicarboxylic acid.

4. The process of claim 1 wherein the oxidation is carried out in the presence of a solvent medium comprising at least 50 weight percent of a $C_{1-3}$ monocarboxylic acid.

5. The process of claim 4 wherein the $C_{1-3}$ monocarboxylic acid is propionic acid.

6. The process of claim 1 wherein the oxidation is carried out in the presence of a solvent medium comprising at least 50 weight percent of benzoic acid.

7. The process of claim 1 wherein the oxidation is carried out in the presence of a catalyst selected from the group consisting of a cobalt catalyst, manganese catalyst, or a combination thereof.

8. The process of claim 7 wherein the catalyst is a mixture of cobalt acetate tetrahydrate and manganese acetate tetrahydrate.

9. The process of claim 1 wherein the oxidation is carried out in the presence of a bromine catalyst.

10. The process of claim 1 wherein the oxidation is carried out in the presence of a cobalt, manganese, and bromine catalyst.

11. The process of claim 1 wherein the oxidation reaction temperature is between about 100° C. and about 240° C.

12. The process of claim 1 wherein the oxidation reaction pressure is between about 10 psig and about 500 psig.

13. The process of claim 10 wherein the oxidation reaction pressure is between about 100 psig and about 200 psig.

14. The process of claim 1 which comprises contacting a para,para'-diisopropyl- or diisobutyl- polyphenyl or an oxidation intermediate thereof with oxygen under reaction conditions sufficient to form the para,para'-polyphenyldicarboxylic acid.

* * * * *